United States Patent [19]
Israel

[11] Patent Number: 5,981,190
[45] Date of Patent: Nov. 9, 1999

[54] ANALYSIS OF GENE EXPRESSION, METHODS AND REAGENTS THEREFOR

[75] Inventor: David I. Israel, Concord, Mass.

[73] Assignee: Ontogeny, Inc., Cambridge, Mass.

[21] Appl. No.: 09/004,192

[22] Filed: Jan. 8, 1998

Related U.S. Application Data

[60] Provisional application No. 60/035,231, Jan. 8, 1997.
[51] Int. Cl.[6] .............................. C12Q 1/68; C12P 19/34; C07H 21/02; C07H 21/04
[52] U.S. Cl. ............................ 435/6; 435/91.2; 536/23.1; 536/24.3; 536/24.31; 536/24.32; 536/24.33
[58] Field of Search ..................... 435/6, 91.2; 536/23.1, 536/24.3, 24.31, 24.32, 24.33

[56] References Cited

U.S. PATENT DOCUMENTS

| 5,508,169 | 4/1996 | Deugau et al. . | |
| 5,695,937 | 12/1997 | Kinzler et al. ............................. | 435/6 |

FOREIGN PATENT DOCUMENTS

| 0 251 283 A2 | 6/1987 | European Pat. Off. . |
| 0 761 822 A2 | 12/1997 | European Pat. Off. . |
| WO 95/20681 | 3/1995 | WIPO . |
| WO 98/14619 | 9/1998 | WIPO . |

OTHER PUBLICATIONS

Kikuya Kato, (1995) Description of the entire mRNA population by a 3' end cDNA fragment generated by class IIS restriction enzymes, Nucleic Acids Research, (18): 3685–3690.

Marc Lemaitre, et al., (1987) Specific antiviral activity of a poly (l–lysine)–conjugated oligodeoxyribonucleotide sequence complementary to vesicular stomatitis virus N protein mRNA initiation site, Proc. Natl. Acad. Sci. USA, 84: 648–652.

Paul Unrau and Kenneth V. Deugau, Non–cloning amplification of specifi DNA fragments from whole genomic DNA digests using DNA 'indexers', AECL Research, Chalk River Laboratories, Chalk River, Ontario K0J 1JO, Canada.

Victor E. Velculescu, et al., (1995) Serial Analysis of Gene Expression, Science 270:484–487.

RNA Polymerase From *E. coli* is a Multisubunit Enzyme, Part V, Genetic Information, RNA Synthesis and Splicing.

Zaug et al, "The tetrahymena ribozyme acts like an RNA restriction endonuclease", Nature 324:429–433, Dec. 1986.

New England Biolabs Catalog, p. 13, Jan. 1996.

*Primary Examiner*—Jeffrey Fredman
*Attorney, Agent, or Firm*—Foley Hoag & Eliot, LLP; Matthew P. Vincent; Diana M. Steel

[57] ABSTRACT

The present invention is directed to methods and reagents for performing rapid, detailed analysis of the spatial and temporal expression of genes. The method uses linker tags in a head to tail array in a serial analysis of gene expression.

22 Claims, 5 Drawing Sheets

ANALYSIS OF GENE EXPRESSION, METHODS AND REAGENTS THEREFOR

This application claims benefit of priority to provisional application 60/035,231 which was filed Jan. 8, 1997.

BACKGROUND OF THE INVENTION

Three important techniques have been developed for nucleic acid manipulation and analysis of genomic sequences.

The first of these is molecular cloning. In its simplest form, this involves first cutting or breaking the target nucleic acid, i.e. DNA, into smaller fragments (typically by restriction endonuclease digestion) and inserting the fragments into a biological vector. The assortment of DNA fragments is then maintained and amplified by the replication of the vector DNA in vivo. Separation of the copies of cloned DNA in this "library" is accomplished by dilution and subsequent growth of bacterial colonies or phage plaques from single organisms bearing copies of only one of the original DNA fragments. Identification of the clones of interest is done by hybridization of a specific labelled probe with the DNA released from each colony or plaque.

More recently, a second technique was developed called the Polymerase Chain Reaction or PCR. This technique can be used to isolate and amplify sequences of interest. The technique allows the definition of any "target" portion of a nucleic acid sequence by the sequences which lie adjacent to it. Consequently, hybridization of nucleic acid primers at these adjacent sites permits the replication of only the intervening target sequence and the adjacent primer sites. The selective amplification by repeated replication in this way results directly in the separation of the desired fragment (or subset of sequences) by effective dilution of all other unwanted sequences by replicated copies of the target sequence. Identification is then carried out by hybridization against a known probe, or more frequently, by simple size analysis by agarose or polyacrylamide gel electrophoresis to confirm that the desired target sequence has been amplified.

A third major technique used for comparative genomic analysis is called Restriction Fragment Length Polymorphism, or RFLP, analysis. Insertions, deletions, and some types of single base substitutions can be detected and their inheritance (and the inheritance of other mutations known to be closely linked) determined. Specific individuals can be uniquely identified from a modification of this technique known popularly as "DNA Fingerprinting". This third technique also begins with restriction endonuclease cleavage of genomic, cloned or PCR-amplified DNA, into fragments. The resulting fragments are separated according to size by gel electrophoresis, and certain target fragments or groups of fragments are identified by hybridization with a specific probe. In this case, the sizes of fragments identified by hybridization with the probe provide a measure of whether the target sequence complementary to the probe is part of an identical or analogous fragment from other individuals.

While each of these three techniques, and the many specific variations which have evolved from them, are extremely valuable in investigating various aspects of structure and organization of particular genes, this analysis represents only one level of genetic complexity. The ordered and timely expression of this information represents another level of complexity equally important to the definition and biology of the organism. Techniques based on complementary DNA (cDNA) subtraction or differential display can be quite useful for comparing gene expression differences between two cell types (Hedrick, et al. (1984) *Nature* 308:149; Liang et al. (1992) *Science* 257:967), but provide only a partial picture, with no direct information about abundance. The expressed sequence tag (EST) approach is a valuable tool for gene discovery (Adams et al. (1991) *Science* 252:1651; Adams et al. (1992) *Nature* 355:632; Okubo et al. (1992) *Nature Genet* 2:173), but like RNA blotting, ribonuclease (RNase) protection, and reverse transcriptase-polymerase chain reaction (RT-PCR) analysis (Alwine et al. (1977) *PNAS* 74:5350; Zinn et al. (1983) *Cell* 34:865; Veres et al. (1987) *Science* 237:415), it evaluates only a limited number of genes at a time.

SUMMARY OF THE INVENTION

The present invention is directed to methods and reagents for performing rapid, detailed analysis of the spatial and temporal expression of genes. In a broad sense, the methods of the present invention are directed to a method for quantifying the amount of a target DNA sequence within a selected RNA or DNA population. In general the subject method can be performed on DNA or RNA samples isolated from any cell, though eukaryotic cells are preferred. Nucleic acid (NA) samples are isolated from sample cells according to a particular criteria, e.g., the nucleic acids are mRNA transcripts or genomic DNA in a particular chemical or physical state. The nucleic acid samples are cleaved to produce a set of TAG fragments where the Tag sequence is derived from the original NA sample, e.g., and collectively are representative of the original NA sample. By ligation of the resulting TAG sequences to one another, concatenated arrays of the TAG sequences can be generated.

In one embodiment, amplification primers can be designed from known gene sequences and used to amplify fragments of the concatemers. For each of the amplification products, the size will depend on the location in the concatemer of the amplification (PCR) primer sequence. Analysis of the number of different amplification products, e.g., the number of different sizes present in the products, permits the quantitation of the frequency of occurrence of that particular TAG sequence in the sample nucleic acid sequence.

The present invention has wide applications, including diagnostic and research uses.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

DETAILED DESCRIPTION OF THE INVENTION

The characteristics of a tissue at any developmental stage are determined by the genes expressed within the various cells in it. The present invention is directed to methods and reagents for performing rapid, detailed analysis of the spatial and temporal expression of 30 genes. The subject method is based at least in part on two principles. First, a short nucleotide sequence tag, e.g., of as little as 9 to 15 base pairs, can contain sufficient information to uniquely identify a gene, provided it is isolated from a defined position within the gene. For example, a sequence as short as 9 bp can distinguish 262,144 transcripts ($4^9$) given a random nucleotide distribution at the tag site, whereas current estimates suggest that even the human genome encodes only about 80,000 transcripts (Fields et al. (1994) *Nature Genet*. 7:345). In another manner of determining the shortest sequence allowing unambiguous identification, it is noted that the complexity of the human genome is about $2 \times 10^9$, approximately 10% of which encodes proteins ($10^5$ different genes at 2000 nucleotides per gene yields $2 \times 10^8$ total sequence. There are $1.1 \times 10^9$ ($4^{15}$) different combinations of sequence in 15 nucleotide stretches.

Second, concatenation of short sequence tags allows the rapid and efficient analysis by amplification methods of the level of gene expression, or the presence of a particular state of a genomic sequence, in a quantified manner.

(i) Overview of the Method

The subject method, generally stated, comprises the isolation of discrete nucleotide sequences which are representative of a nucleic acid library, e.g., of a cDNA or genomic library. The isolated sequences can be sub-cloned into a system which permits the sequences to be amplified. Preferably, the isolated sequences are concatenated with one another to form concatemers of sequences which, as described below, permit the indexing of the nucleic acids sequences from the original population, and the quantification of relative populations. Various embodiments of the subject method are described below.

According to FIG. 1, in certain embodiments the subject method can be performed as follows. Nucleic acid (NA) samples (1) are isolated from sample cells according to a particular criteria, e.g., the nucleic acids are mRNA transcripts or genomic DNA, or some sub-population thereof. The cells can be, for example, mammalian cells, particularly human cells, from embryonic or adult origin. In certain embodiments, the nucleic acid samples can be linked to a soluble or insoluble support (2). In the illustrated embodiment, this can be accomplished using standard oligo-dT derivatized beads. The nucleic acid samples are then cleaved with an anchoring enzyme(s) (AE) ideally selected to predictably cut all or a substantial population of the sample nucleic acid molecules at a predetermined sequence to produce cleaved NA (3). A linker nucleic acid (4) is ligated to the newly created ends of the resulting cleaved NA (3) to produce the chimeric linker-NA (5). That set of molecules are then cleaved with a tagging enzyme (TE) which cuts the sample nucleic acid at some distance 3' to the linker nucleic acid sequence to produce the linker-TAG fragment (6), e.g., where the Tag sequence (6a) is derived from the original NA sample. By blunt end ligation of the linker-NA itself, or after the further addition of a second linker sequence at the 3' end, providing a restriction site, or by blunt end ligation. The linker-NA fragments are ligated to form concatenated nucleic molecules (7).

In certain embodiments, the concatemers are sequenced, e.g., by any of a number of sequencing methods known in the art. For instance, Sanger or Maxam and Gilbert sequencing can be performed. In other embodiments, the sequence can be obtained by techniques utilizing capillary gel electrophoresis or mass spectroscopy. See, for example, U.S. Pat. No. 5,003,059. Such techniques are preferred for automation of the sequencing step.

In other embodiments, the concatemers can be used to quantitate the level of expression of a gene or genes. Based on the sequence at which the anchor enzyme cleaves, amplification primers (8) can be designed from known gene sequences, e.g., by selection of sequences immediately 3' to the AE cleavage sequence in a gene of interest. Using amplification techniques dependent on the amplification primers, e.g., such as either Anchor PCR or RACE PCR, fragments of the concatemers (7) can be amplified. In the particular illustration of FIG. 1, each of the PCR amplification products correspond in size to the distance between the location in the concatemer of the amplification primer (8), e.g., the TAG sequence of interest, and the site of a generic primer (9) which corresponds to a vector sequence. In RACE PCR, each amplification product would correspond in size to the distance between the amplification primer and the end of a linearized concatemer.

Analysis of the population of amplification products, such as by chromatographic separation of the amplification products based on size, provides a "quantum" number corresponding to the number of times the amplification primer sequence occurs in the concatemer. This number, in turn, reveals the frequency of the selected nucleic acid sequence (of the amplification primer) in the sample nucleic acid derived from the cell sample. In the case where the sample nucleic acids are mRNA transcripts, the quantum number reveals the level of expression of a particular transcript. Thus, the subject method allows easy quantification of the level of expression of a gene. In the case of genomic DNA selected on the basis of a particular criteria, e.g., such as nuclease sensitivity or methylation, the quantum number reveals the relative percentage of that state for a given genomic sequence in a sample of cells.

Figure 2A:
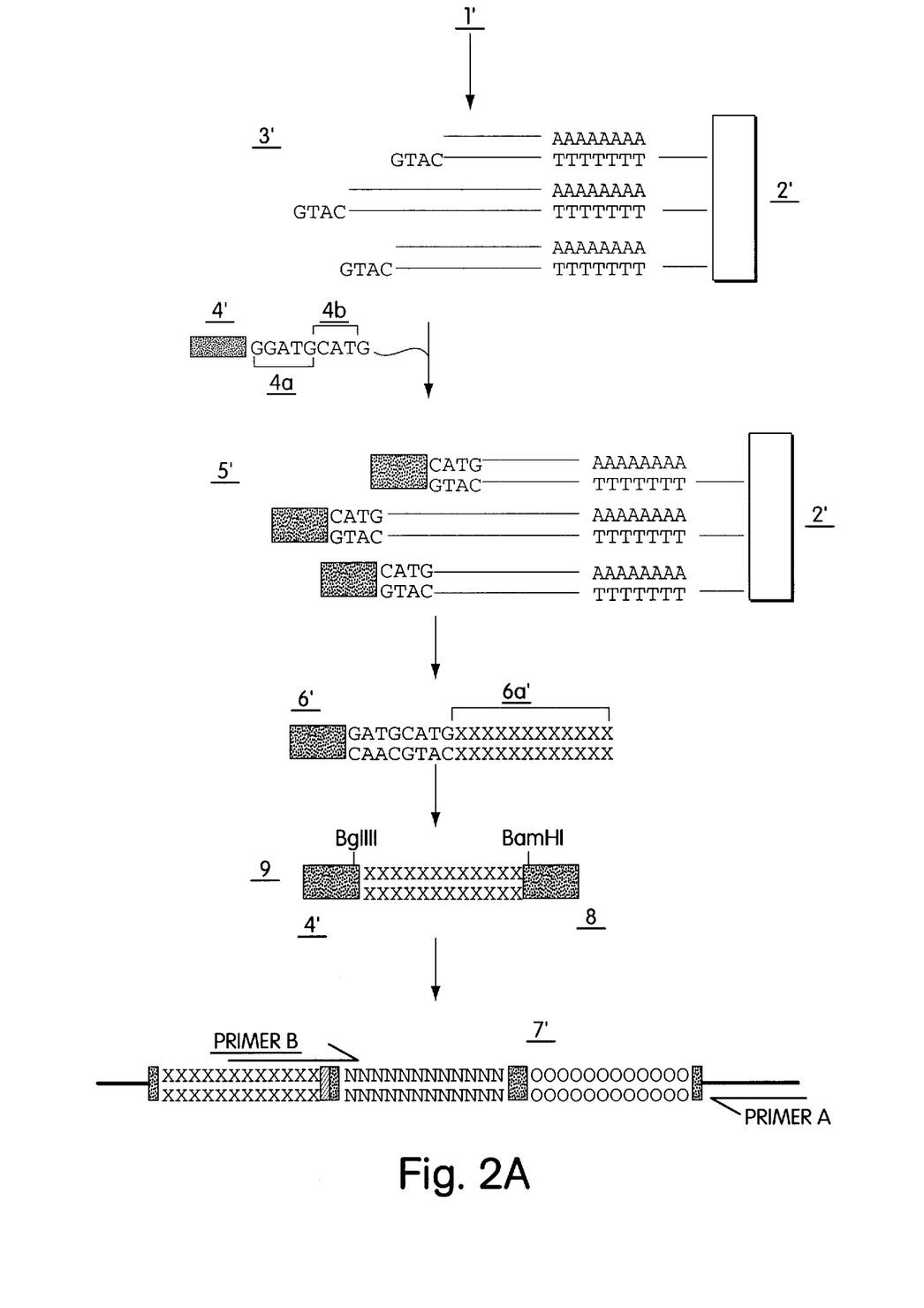

FIG. 2A shows, in an exemplary embodiment, how these principles can be implemented for the analysis of mRNA expression. Double-stranded cDNA (1') is synthesized from mRNA by means of a biotinylated oligo(dT) primer. The cDNA is then cleaved with a restriction endonuclease (anchoring enzyme) that would be expected to cleave most transcripts at least once. Typically, restriction endonucleases with 4-bp recognition sites will be used for this purpose because they cleave every 256 bp ($4^4$) on average, whereas most transcripts are considerably larger. The most 3' portion of the cleaved cDNA (3') is then isolated by binding to oligo-dT streptavidin beads (2'). This process provides a unique site on each immobilized transcript that corresponds to the restriction site located closest to the polyadenylate poly(A) tail.

The cleaved cDNA is ligated to a linker (4') that contains (i) a type IIS restriction site (4a) that is recognized by a tagging enzyme such as BsmF1, and (ii) a restriction endonuclease site (4b) such as a BglII site. Type IIS restriction endonucleases cleave at a defined distance up to 20 bp away from their asymmetric recognition sites (Szybalski (1985) Gene 40:169). The linkers are designed so that cleavage of the ligation products with the tagging enzyme results in release of the linker with a short piece of the sample cDNA (the linker-TAG fragment, 6').

For example, FIG. 2A shows a combination of anchoring enzyme and tagging enzyme that would yield a 12-bp TAG sequence (6a') in the linker-TAG fragment. To the blunt ends created by the tagging enzyme, a second linker sequence (8) is ligated to the linker-TAG fragment to form a linker-TAG-linker (9). In the illustrated embodiment, the second linker provides another restriction endonuclease site which will produce a sticky end complementary to that produced by the endonuclease restriction site of the first linker. In the illustrated method of FIG. 2A, the second linker includes a BamH1 site. As an optional step, the first and second linkers serve as sites for PCR amplification of the linker-TAG-linker construct. After treatment of the resulting DNA fragment with the restriction enzymes which appropriately cleave both the first and second linkers, the linker-TAG-linker fragments (9) are ligated to form concatenated nucleic molecules (7'). BamHl and BglII produce compatible sticky ends. In the illustrated example, by carrying out the ligation in the presence of BamHl and BglII, the resulting concatemer will result in the linker-NA fragments being linked in a head-to-tail format by virtue of the redigestion of BamHI/BamHI and BglII/BglII ligation products but not of the BamHI/BglII ligation products (which do not produce a sequence recognized by either restriction enzyme).

The concatemer arrays can be isolated, preferably as 2-3 kb fragments, and ligated into an amplification vector to produce a variegated library of the concatemer arrays. The library will preferably include a sufficient number of different concatemers to provide an overall population of TAG sequences that is representative of the population of sample nucleic acid isolated from the cells. Using a set of PCR primers corresponding to (i) a sequence in the amplification vector (primer A in FIG. 2A), and (ii) a TAG sequence from a gene (primer B in FIG. 2A; e.g., selected by virtue of the knowledge of the anchor enzyme cleavage site in the gene), PCR amplification can be carried out with the concatemer array library. As illustrated in FIG. 2A, the occurrence of the TAG sequence of a particular gene in a concatemer gives rise to a PCR product of discrete size which corresponds to the distance in each concatemer of the library between primer A and each occurrence of the selected TAG sequence (primer B). Analysis of the PCR products by, for example, electrophoresis will reveal, by generation of a ladder of PCR products, how many times the selected TAG sequence occurs in the library, e.g., it will provide a quantum number for occurrence. The frequency of occurrence of the gene in the mRNA pool can then be calculated by dividing that quantum number by the estimated total number of TAG sequences in the library. Appropriate controls can include the determination of the quantum number and frequency of occurrence for, e.g., an mRNA known to be expressed, or by incorporation of predetermined amount of a control TAG sequence during formation of the concatemers.

In another embodiment, the concatemer-containing vector is linearized, e.g., by cleavage at the site immediately 3' to the concatemer array. Utilizing a primer for the TAG sequence of interest, RACE PCR can be employed to generate PCR products. The size of each PCR product is the distance between the occurrence of a selected TAG sequence in each concatemer of the library, and the 3' end of the linearized vector.

In still another embodiment, after the above-described step of cleaving the immobilized cDNA with an anchoring enzyme, the cleaved cDNA is then divided into two pools, with each pool being ligated to a one of two different linkers containing a type IIS restriction site. See FIG. 2B. Each pool is treated with the type IIs enzyme to release a blunt-ended linker-TAG fragment. The two pools are then remixed under conditions wherein the linker-TAG fragments from each pool are blunt-end ligated to one and other to form head-to-head "diTAGs" (10). The ligated TAGs then served as templates for polymerase chain reaction (PCR) amplification with primers specific to each the two different linkers. This step serves purposes in addition to allowing amplification of the TAG sequences. For instance, it provides a means to completely eliminate potential distortions introduced by PCR. Because the probability of any two TAGs being coupled in the same diTAG is small, even for abundant transcripts, repeated diTAGs potentially produced by biased PCR could be excluded from analysis without substantially altering the final results. Cleavage of the PCR product with the anchoring enzyme allows isolation of diTAGs that can then be concatenated by ligation.

Figure 2B:
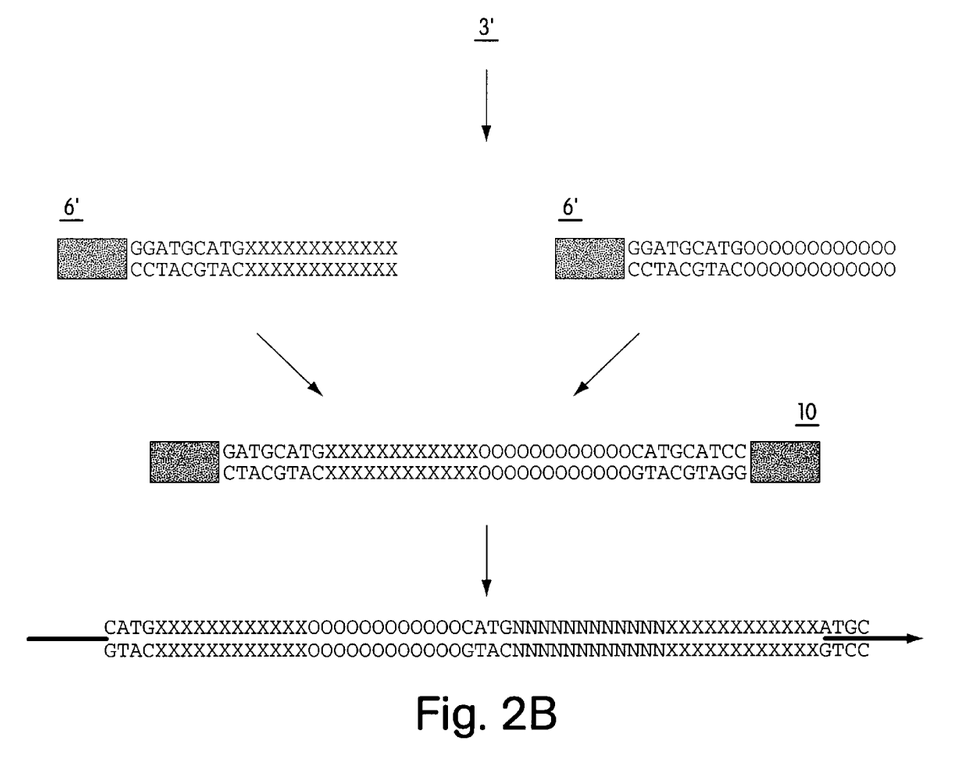

PCR analysis of the head-to-head diTAGs produced by the latter embodiment deserves mention. Briefly, because the TAG sequence of interest from a particular gene can occur in either orientation, the PCR primers should include a set of anchor primers for amplifying the TAG sequence in either orientation. As illustrated in FIG. 2B, the PCR reaction can include the two complementary TAG sequence primers, and two primers corresponding to either the 3' or 5' ligation sites of the concatemer in the vector. The amplification products will produce a quantum number, though it must be calculated by accounting for the amplification of sequences between any two complementary TAG sequence primers. For instance, two occurrences of the TAG sequence in the concatemer will produce, in the exemplary embodiment, a ladder of six PCR products. Likewise, three occurrences produces twelve different product, four produces twenty, five produces thirty, and so on, e.g., $(n^2+n)$ where n is the number of occurrences in the array.

Figure 1:
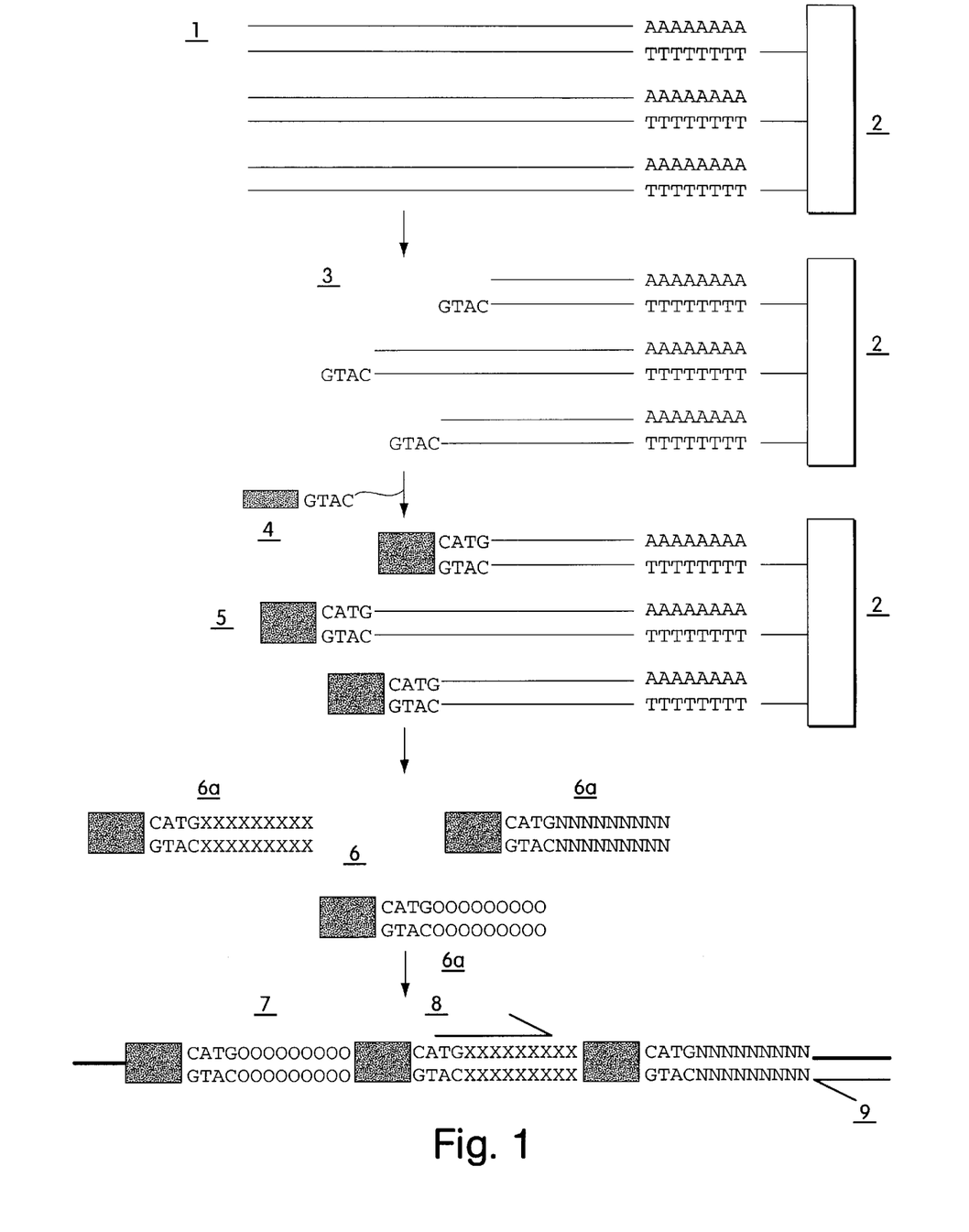
FIGS. 1, 2A, 2B, 3, and 4 are schematic representations of aproaches to analyzing nucleic acid content by the subject method.
Figure 3:
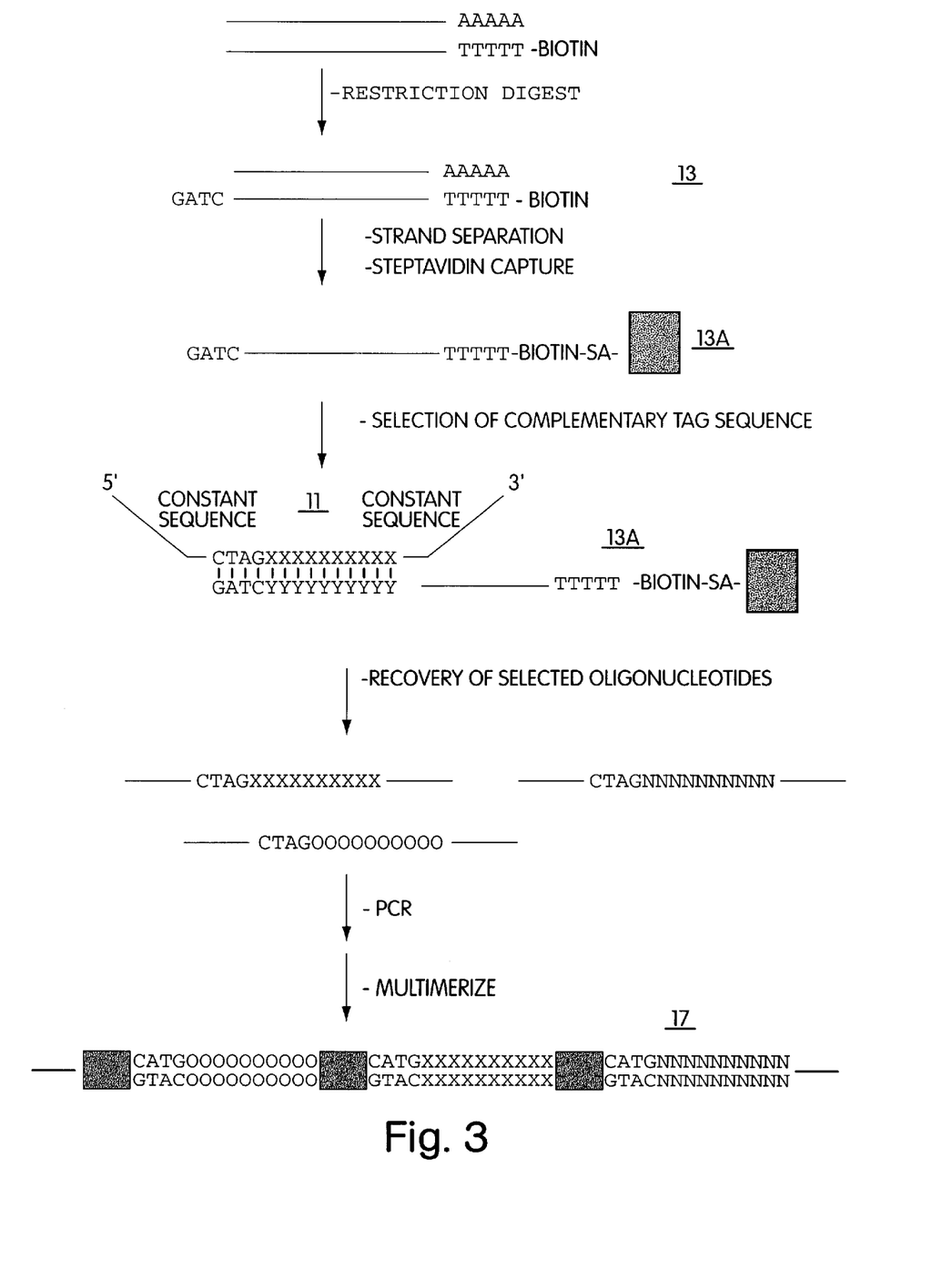

FIG. 3 illustrates a version of another embodiment for isolating the linker-TAG fragment (6) of FIG. 1. Briefly, this embodiment relies on isolating oligonucleotides, e.g., from a variegated mixture of oligonucleotides, by their ability to uniquely hybridize to single stranded sequences exposed in the nucleic acid sample. As illustrated, nucleic acid samples, in this case cDNA, are cleaved at some internal site to produce the cleaved NA (13). The duplex is then separated to give single-stranded DNA, and one of the strands is isolated. In the illustrated example, the second strand of the cDNA is synthesized with a biotin-oligo-dT tail which permits capture of that strand by a streptavidin medium.

The isolated single-stranded NA fragment (13A) can then be contacted with a library of potentially complementary "tagging" oligonucleotides (11) under sufficiently stringent conditions that only those tagging oligos with perfect or near-perfect complementarity (e.g., no more than 1 or 2 mismatches) over a stretch of 12 or more nucleotides will remain annealed. In the illustrated embodiment, the tagging oligo (11) library is represented by the general formula X-AE'-(N)$_p$-Y, where: AE' represents a sequence complementary to the anchor enzyme cleavage site of the single-stranded NA fragment (13A); each N independently represents a nucleotide A, T, G or C, or an analog thereof; p is an integer of 4 or greater (e.g., so that AE'-N$_p$ is 9-100 nucleotides in length, though more preferably 9–50, 9–25 or 9–15); and X and Y represent 5' and 3' flanking sequences which can provide, inter alia, sites for PCR primers or cleavage sites for restriction enzymes.

Those Tagging Oligos (11) in which the AE'-(N)$_p$ sequence are complementary to the NA fragment (13A) are recovered after hybridization. Optionally, though preferably, the recovered Tag Oligos are amplified, e.g., by PCR or by sub-cloning into amplifiable vectors. By including restriction cleavage sites in the flanking X and Y sequences of the Tagging Oligo, or complementary X and Y sequences, concatemers (17) of the isolated sequences can be generated and utilized as above.

In still another embodiment, in place of the tagging enzyme shown in FIG. 1, random cleavage of the chimeric linker-NA (5) can be carried out to isolate a population of linker-TAG fragments. For instance, the cleavage can be carried out by limited enzymatic or chemical cleavage, as for example by limited treatment with a random exonuclease such as DNase I, or by the chemical cleavage method of Maxam and Gilbert (1977) *PNAS* 74:560. The resulting linker-TAG fragment can be amplified in vectors, by PCR and/or used to generate the above concatemers.

This embodiment is likely to produce a heterologous population of linker-TAG fragments with respect to size. Accordingly, in preferred embodiments, linker-TAG fragments of certain sizes, e.g., 9–25 nucleotides, can be isolated by such techniques as size exclusion chromatography.

Figure 4:
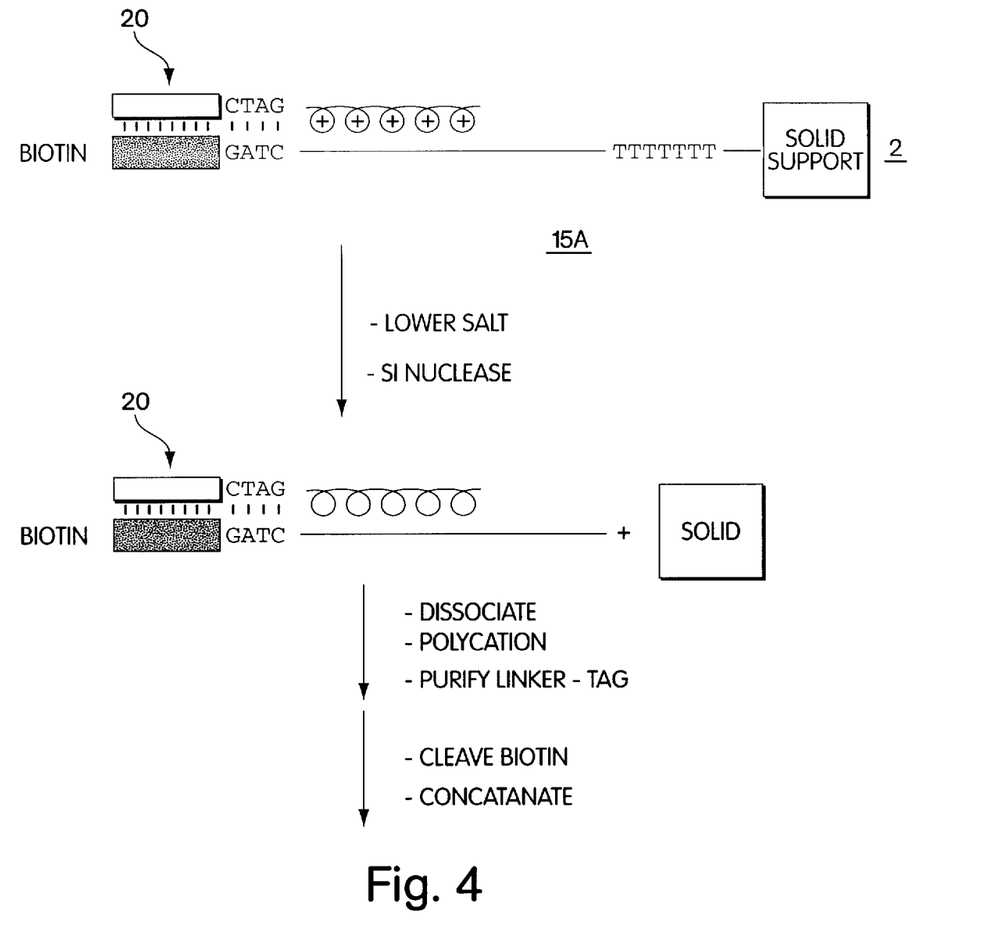

In still another embodiment, rather than random cleave the chimeric linker-NA (5) as described above, DNase protection and other "foot printing" type methods can be adapted to create a more homogenous size in the resulting linker-TAG fragments. As illustrated in FIG. 4, an anchor oligonucleotide (20) can be designed which hybridizes to the common linker sequence of a single-stranded chimeric linker-NA (15A). The anchor oligonucleotide is associated, e.g., covalently or non-covalently, with a polypeptide or other large molecule (such as other polymers) which can non-specifically associate with DNA. For instance, the anchor oligonucleotide may be covalently linked with a polymer having many cationic groups (e.g., which are positively charged under the reaction conditions).

Merely to illustrate, the anchor oligonucleotide is covalently linked to poly-lysine of suitable size to bind 9–15 nucleotides simultaneously. Under high salt concentrations, the anchor oligonucleotide will selectively bind to the linker nucleic acid sequence, whereas the poly-lysine will contribute little to the binding of the DNA. With the poly-lysine now localized near the linker sequence, the salt is lowered to favor DNA binding by the poly-lysine. The complex is then subjected to enzymatic or chemical cleavage condition which will hydrolyze substantially all single-stranded DNA. It may be desirable, therefor, that the linker nucleic acid added to the cleaved NA be non-hydrolyzable as the anchor oligonucleotide may not effectively protect that sequence under low salt conditions. The resulting digestion product should include a relatively homogenous size population of linker-TAG fragments which can be further manipulated as above.

In other embodiment, rather than capture the cDNA, for example, by the poly(A) tail, cDNAs can be captured by, e.g., 7 mG caps, or by amplification using a set of degerate primers for the conserved start ATG and flanking Kozak sequence. In those embodiment, the cleaved NA product would be a 5' fragment of the cDNA.

In the case of genomic DNA, the sample nucleic acid can be separated on the basis of a chemical or physical state of the DNA, e.g., based on the methylation state, chromatin condensation state, etc. The separation can itself be by physical or chemical means. In an illustrative embodiment, genomic DNA is treated with DNase I. Decondensed portions of the genomic DNA will be cut more often by the nuclease than condensed portions (Galas et al. (1987) *Nucleic Acids Res.* 5:3157). The genomic DNA is then fractionated by size, with smaller fragments (e.g., less than about 2–5 kb) being isolated. These fragments are then cleaved with an anchor enzyme, ligated to a linker, cleaved again with a tagging enzyme, and ligated to form concatemers of TAG sequences derived from nuclease sensitive genomic DNA. Based on the anchor enzyme recognition sequence, PCR primers can be designed by genomic DNA sequences of known genes, e.g., from transcriptional regulatory regions, from coding sequences, or from intronic sequences.

The subject method can provide both quantitative and qualitative data about gene expression and/or the state of genomic sequences. For instance, in illustrative embodiments, the combination of different anchoring enzymes with various recognition sites and type IIS enzymes with cleavage sites 5 to 20 bp from their recognition elements lends great flexibility to this strategy. Similar flexibility is accorded by the other methods for creating representative TAG sequence populations. As efforts to fully characterize the genome near completion, the subject method should allow a direct readout of expression levels and genomic states of genes in any given cell type or tissue at various developmental stages or disease states. Any laboratory with the capability to perform PCR could perform the subject method for this purpose.

It is expected that the subject method will be widely applicable to speed the discovery of how gene expression may be involved in a variety of normal and disease states, including proliferative and developmental disorders, as well as to interpret the large amounts of gene sequence data coming from the Human Genome Project. It also understood that the subject method will provide new insights into the control of normal development.

Use of different anchoring enzymes will ensure that virtually all transcripts of the desired abundance can be identified in the present method. The genes encoding those tags shown to be most interesting on the basis of their differential representation can be positively identified by a combination of database searching and amplification analysis. Obviously, the subject method can be applied to the analysis of organisms other than humans and could direct investigation toward genes expressed in specific biologic states.

(ii) Definitions

For convenience, certain terms employed in the specification and claims are collected here.

As used herein, the term "nucleic acid" refers to polynucleotides such as deoxyribonucleic acid (DNA), and, where appropriate, ribonucleic acid (RNA).

As used herein, the term "vector" refers to a nucleic acid molecule capable of transporting another nucleic acid to which it has been linked. Preferred vectors are those capable of autonomous replication. In the present specification, "plasmid" and "vector" are used interchangeably as the plasmid is the most commonly used form of vector. Moreover, the invention is intended to include such other forms of amplification vectors which serve equivalent functions.

"Complementary DNA" or a "cDNA" as used herein includes recombinant genes synthesized by reverse transcription of mRNA and from which intervening sequences (introns) have been removed.

"Primer" as used herein refers to an oligonucleotide, preferably an oligodeoxynucleotide, which possesses a free 3'OH group which, upon hybridization to a nucleic acid template, is recessed relative to the 3' end of the template and thus is capable of acting as a site of initiation of the synthesis or polymerization of a nucleic acid polymer, the sequence of which is complementary to the template strand, in the presence of deoxynucleotide substrates, an appropriate enzyme capable of DNA replication, and a suitable temperature and pH. Primers that consist of the same sequence or very similar sequence as a target nucleic acid are said to be "complementary" with respect to that target nucleic acid.

"Amplification" as used herein refers to an increase in the amount of the pre-existing nucleic acid template.

The term "representative of a nucleic acid library" means all, or a substantial portion of a population of nucleic acid sequences which can be thought of as discrete sequences.

The term "polymeric support" as used herein, refers to a soluble or insoluble polymer to which nucleic acid can be covalently or non-covalently attached. Many suitable polymeric supports are known, and include soluble polymers such as polyethylene glycols or polyvinyl alcohols, as well as insoluble polymers such as polystyrene resins. A polymeric support is termed "soluble" if linkage of a nucleic acid with the polymeric support results in a soluble polymer-supported nucleic acid under the conditions employed. A polymeric support can be soluble under certain conditions and insoluble under other conditions. A polymeric support is termed "insoluble" if the nucleic acid-linked polymer is insoluble under the conditions employed.

The term "chromatographic" with respect to separation techniques used herein refers to methods of separating amplification products on the basis of size. Chromatography can include, for example, size exclusion chromatography, both normal phase and reversed-phase high performance liquid chromatography (HPLC), capillary electrophoresis (CE), and chromatofocusing.

The term "variegated population of nucleic acids" means a library of nucleic acids having diversity in the sequences of the individual members which make up the library.

The term "variegated concatenated array" means a library of nucleic acids having diversity in the sequences of the individual members which make up the library.

The term "gross amplification" refers to the amplification, e.g., catalytically, of a nucleic acid molecule without the full sequencing of the molecule.

The term "substantial portion of the nucleic acid molecules of the sample" refers to a population of nucleic acids which is statistically representative of the sample. In preferred embodiments, a substantial portion of the nucleic acid molecules of the sample will include sequences for at least 75% of the sample, more preferably 80%, 85%, 90%, 95% or even 98% of the sample.

(iii) Isolation of Sample Nucleic Acid

The sample nucleic acid which is analyzed by the subject method can be isolated from any cell or collection of cells. For instance, the nucleic acids can be isolated from the cells of either adult tissue or organs or embryonic tissue or organs at any given developmental stage (including oocyte, blastocyte, etc.). The cells can be derived from healthy tissue or diseased tissue. In the case of a solid organ, the cell sample can be obtained by, e.g., biopsy. For blood, lymph and other bodily fluids, the cells can be isolated from the fluid component, e.g., by filtration, affinity purification, centrifugation or any other technique known in the art. The cells can be isolated to include a specific subset of phenotypes of cells from a given tissue, or can be derived to include all or a substantial portion of cells representative of the tissue. For instance, the cells can be derived from an organ where the cells are particularly of epithelial, mesenchymal or endothelial origin. Subsets of cells can be isolated, for example, by use of cell surface markers or careful sectioning of a tissue.

There are a variety of methods known in the art for isolating RNA from a cellular source, any of which may be used to practice the present method. The Chomczynski method, e.g., isolation of total cellular RNA by the guanidine isothiocyanate (described in U.S. Pat. No. 4,843,155) used in conjunction with, for example, oligo-dT streptavidin beads, is an exemplary mRNA isolation protocol. The RNA, as desirable, can be converted to cDNA by reverse transcriptase, e.g., poly(dT)-primered first strand cDNA synthesis by reverse transcriptase, followed by second strand synthesis (DNA pol I).

Likewise, there are a wide range of techniques for isolating genomic DNA which are amenable for use in a variety of embodiments of the subject method. In preferred embodiments, it will be desirable to isolate only a portion of the total genomic DNA on the basis of the chemical and/or physical state in which it is present in a collection of cells. For instance, transcriptionally active and/or potentially active genes can be distinguished by several criteria from inactive sequences. In higher eukaryotes, gene activation is accompanied by an increased general sensitivity to endonucleases like DNase I or micrococcal nuclease. This increased sensitivity probably reflects both the partial decondensation of chromatin. In addition, gene activation usually causes a coreplication domain that extends much beyond the decondensation domain. Chromatin digestion by DNase I, for example, will produce smaller digestion fragments from those areas of the genome which have undergone decondensation relative to areas of condensed chromatin structure (Galas et al. (1987) *Nucleic Acids Res.* 5:3157), e.g., the smaller fragments will be enriched for genomic sequences from genes in activated states.

Likewise, changes in methylation status of a gene provides another mechanism by which potential for expression can be altered. Thus, genomic DNA can be treated with methyl-sensitive restriction enzymes (such as DpnI) in order to produce endonuclease fragments of genes dependent on the methylation state of the surrounding genomic sequences.

(iv) Selection of Anchor Enzyme and Tagging Enzyme

There are a wide variety of choices for the anchor enzyme used to create the cleaved NA (3). One general criteria concerns the predictability with which the enzyme cleaves the nucleic acid, e.g., the ability to recognize a predefined sequence (AE sequence) so that amplification primers can be designed for latter steps. Another criteria relates to the frequency of occurrence of the AE sequences in the population of sample nucleic acids. As set out above, it will often be desired that the anchor enzyme cut with enough frequency that, statistically, a substantial portion of the nucleic acid molecules of the sample include at least one AE sequence. In one embodiment, the AE is comprised of one or more restriction endonucleases. In a preferred embodiment, the restriction endonuclease(s) is a 4 base cutting enzyme, such as AciI, AluI, BfaI, BstUI, DpnI, DpnII, HaeIII, HhaI, HinPlI, HpaII, MboI, MseI, MspI, RsaI or others known in the art (many of which are commercially available). Many other restriction enzymes of longer sequence specificity are also known and may be used, as appropriate. Digestion of a DNA molecule with a selected restriction enzyme is a well-known process, where the optimum digestion conditions are specified by the enzyme manufacturer. A generic restriction enzyme process for use is given by J. Sambrook et al., Molecular Cloning, pp. 5.28–5.33, Cold Spring Harbor Laboratory Press (1989).

Other methods for cleaving the sample nucleic acid at predetermined sequences include the use of ribozymes and oligonucleotide-tethered nucleases.

Still another example of a technique for targeted cleavage of the sample nucleic acid utilizes the "reversal of splicing" reaction described in the Jarrell U.S. Pat. No. 5,498,531 with the use of Y-branched introns as the anchor enzyme. As described by the Jarrell patent, both group I and group II introns can integrate into foreign RNAs by reversal of the self-splicing reactions. In each case, the reversal of intron splicing is dependent on a sequence in the RNA transcript which is complementary to a sequence in the intron. According to the method of the Jarrell patent, RNA isolated from the sample cells is mixed with a 2'–5' Y-branched intron. The reverse-splicing is initiated by binding of the intron binding site (IBS) of the RNA to an exon binding sequence (EBS) of the Y-branched intron, followed by nucleophilic attack by the 3'-OH of the exon on the 2'–5' phosphodiester bond of the branch site. This reaction, results in the cleavage of the RNA, with addition of each half of the Y-branched intron to the two portions of the cleaved RNA. Thus, not only does the Y-branched intron serve the role of an anchor enzyme, the added sequence from the intron can be used as a linker. The sequence of the EBS is generally 3 to 8 consecutive residues, and its sequence can be altered, e.g., the only criteria is that the IBS be complementary. Likewise, other portions of the Y-branched intron can be altered, e.g., to provide restriction enzyme recognition sites for the TE. After reaction, the resulting RNA is reverse transcribed to DNA, and utilized as described above.

Similarly, a variety of reactions are available for generation of the TAG sequence by a tagging enzyme. As set out above, the tagging enzyme is preferably one which recognizes a sequence (TE sequence) in the linker/AE sequence and cleaves at a site distal to the TE sequence to produce a fragment including at least 8 (e.g. 8–30) nucleotides of TAG sequence. Exemplary tagging enzymes include the group II restriction enzymes, many of which are available from commercial sources, including BbsI, BbvI, BcgI, BsgI, BsmFI, FokI, HgaI, HphI, MboII, MnlI, and SfaNI.

(v) Selection of Immobilizable Support

Soluble polymeric supports include functionalized polymers based on polyvinyl alcohol or polyethylene glycol (PEG). A soluble support can be made insoluble (e.g., can be made to precipitate) by addition of a suitable inert nonsolvent. One advantage of reactions performed using soluble polymeric supports according to the invention is that reactions (such as cleavage by a restriction enzyme) in solution can be more rapid, higher yielding, and/or more complete than reactions that are performed on insoluble polymeric supports.

Insoluble polymeric supports include, e.g., functionalized polymers based on polystyrene, polystyrene/divinylbenzene copolymers, and other polymers known to the skilled artisan.

(vi) Chromatographic Techniques

It will be recognized that the separating step of the present method may be accomplished by any number of techniques and methods which will separate the amplification products by size. Examples include but are not limited to gel electrophoresis, capillary electrophoresis, chromatography, pulsed field gel electrophoresis and mass spectrometry. Thus, one skilled in the art will recognize that the separation of amplification products can be done by a variety of methods. The choice of method will depend on a number of factors, such as the available laboratory equipment, the amount of amplification product present, the label if any, the dye, the preference of the party performing the testing, convenience and the like.

Capillary electrophoresis allows the rapid separation of DNA fragments through tiny polyacrylamide gels in thin capillaries. The chief advantage is that much larger voltages can be applied and resolution is enhanced. The process can be automated. Once tubes are loaded, electrophoresis and data acquisition can be automated by direct connection to computer. An example includes the Model 270A-HT High Throughput Capillary Electrophoresis System (Applied Biosystems). Instead of bands on a gel, the DNA fragments are represented by spikes as a function of time indicating the presence of different molecules of different sizes. PCR-generated spike patterns be quickly obtained with greater resolution of different-sized fragments.

Non-electrophoresis methods, namely chromatography, can be used to separate PCR-generated DNA fragments by size. High-Performance Liquid Chromatography (HPLC) methods can be used to separate DNA fragments by the use of size-exclusion columns (Series 800 HRLC Gradient System-BioRad). DNA fragments are represented by spikes as a function of time and the data is digitized and fed directly to a computer. Electrophoresis methods, however, are usually preferred because of greater reliability and resolution.

One skilled in the art will recognize that measurement of the pattern of sized amplification products to determine the quantum number for a transcript or gene may also be accomplished by several means, direct visualization or by automation using a bar code reader, a laser reader, digitizer, a photometer, a fluorescence reader or computer planimetry. The choice of measurement method depends in part on the separation step and available instrumentation.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method for detecting the presence of a selected nucleotide sequence in a nucleic acid sample, comprising
   (i) isolating discrete nucleotide sequences representative of a nucleic acid sample, by
      (a) cleaving, at a first cleavage site, the nucleic acids of the sample to produce cleaved nucleic acids,
      (b) ligating a linker nucleic acid sequence to the cleaved nucleic acids to produce chimeric linker nucleic acids of the general formula L—N, wherein L is the linker nucleotide sequence and N is a sample nucleotide sequence from the nucleic acid sample,
      (c) cleaving, at a second cleavage site, the chimeric linker nucleic acids within the sample nucleotide sequence to produce linker-TAG fragments of the general formula L—N', wherein L is the linker nucleotide sequence and N' is a portion of the nucleic acid sequence N,
   (ii) ligating the linker-TAG fragments to form variegated head to tail concatenated arrays, and
   (iii) determining the number of occurrences of a selected nucleotide sequence in the concatenated arrays.

2. The method of claim 1, wherein the number of occurrences of a selected nucleotide sequence in the concatenated arrays is determined by PCR amplification using primers for the selected nucleotide sequence.

3. The method of claim 1, wherein the nucleic acid sample includes genomic DNA.

4. The method of claim 1, wherein the nucleic acid sample includes cDNAs.

5. The method of claim 1, wherein the cleaved nucleic acids are enriched, before cleaving to produce the linker-TAG fragments, for nucleic acids having first cleavage sites other structural elements of the cleaved nucleic acids positioned such that the enriched linker-TAG fragments share size similarity.

6. The method of claim 5, wherein the cleaved nucleic acids are enriched for nucleic acids including poly(A) or poly(T) tails.

7. The method of claims 1 or 5, wherein the nucleic acid of the sample are enzymatically cleaved at the first cleavage site.

8. The method of claim 7, wherein the nucleic acids of the sample are cleaved with an enzyme having a recognition sequence which cleaves a substantial portion of the nucleic acids at least once.

9. The method of claim 7, wherein the anchoring enzyme is a restriction endonuclease.

10. The method of claim 9, wherein the anchoring enzyme is selected from the group consisting of AciI, AluI, BfaI, BstUI, DpnI, DpnII, HaeII, HhaI, HinPII, HpaII, MboI, MseI, MspI and RsaI.

11. The method of claim 1, wherein the anchoring enzyme is a ribozyme.

12. The method of claim 1, wherein the N' represents from 4–100 nucleotides.

13. The method of claim 1, wherein the chimeric linker nucleic acids are cleaved at the second cleavage site with a restriction enzyme.

14. The method of claim 13, wherein the restriction enzyme is a group II restriction enzyme.

15. The method of claim 14, wherein the group II restriction enzyme is selected from the group consisting of BbsI, BbvI, BcgI, BsgI, BsmFI, FokI, HgaI, HphI, MboII, MnII and SfaNI.

16. The method of claim 1, wherein the chimeric linker nucleic acids are cleaved in a footprinting assay at a second cleavage site, while a molecule binds to and protects the N' nucleotide sequence from cleavage.

17. The method of claim 16, wherein the molecule which binds to and protects the N' nucleotide sequence from cleavage is a polycationic polymer.

18. The method of claim 1, wherein a concatenated array is represented by the general formula —(L—N')$_z$—, wherein L—N', for each occurrence in the concatenated array, represents a linker-Tag fragment from the nucleic acid sample, and z is an integer of 2 or greater.

19. The method of claims 1, 18 or 19, wherein a concatenated array includes from 50 to 1000 different nucleic acid sequences N'.

20. The method of claim 7, wherein the nucleic acid sample includes from 100 to $10^6$ different contiguous nucleic acid sequences.

21. The method of claim 1, wherein the N' represents from 9–15 nucleotides.

22. The method of claim 1, wherein the N' represents from 9–25 nucleotides.

\* \* \* \* \*

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 13 base pairs
        (B) TYPE: nucleic acid
        (C) STRANDEDNESS: single
        (D) TOPOLOGY: linear     (ii) MOLECULE TYPE: other nucleic acid     (xi) SEQUENCE DESCRIPTION: SEQ ID NO:1:

CATGNNNNNN NNN                                          13

(2) INFORMATION FOR SEQ ID NO:2:

(i) SEQUENCE CHARACTERISTICS:
        (A) LENGTH: 13 base pairs
        (B) TYPE: nucleic acid
        (C) STRANDEDNESS: single
        (D) TOPOLOGY: linear     (ii) MOLECULE TYPE: other nucleic acid     (xi) SEQUENCE DESCRIPTION: SEQ ID NO:2:

GTACNNNNNN NNN                                          13

(2) INFORMATION FOR SEQ ID NO:3:

(i) SEQUENCE CHARACTERISTICS:
        (A) LENGTH: 9 base pairs
        (B) TYPE: nucleic acid
        (C) STRANDEDNESS: single
        (D) TOPOLOGY: linear     (ii) MOLECULE TYPE: other nucleic acid     (xi) SEQUENCE DESCRIPTION: SEQ ID NO:3:

GGATGCATG                                                  9

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid     (xi) SEQUENCE DESCRIPTION: SEQ ID NO:4:

GATGCATGNN NNNNNNNNNN                                20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid     (xi) SEQUENCE DESCRIPTION: SEQ ID NO:5:

CAACGTACNN NNNNNNNNNN                                20

(2) INFORMATION FOR SEQ ID NO:6:

(i) SEQUENCE CHARACTERISTICS:
        (A) LENGTH: 21 base pairs
        (B) TYPE: nucleic acid

```
        (C) STRANDEDNESS: single
        (D) TOPOLOGY: linear (ii) MOLECULE TYPE: other nucleic acid (xi) SEQUENCE DESCRIPTION: SEQ ID NO:6:

GGATGCATGN NNNNNNNNNN N                                              21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

CCTACGTACN NNNNNNNNNN N                                              21

(2) INFORMATION FOR SEQ ID NO:8:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

GATGCATGNN NNNNNNNNNN NNNNNNNNNN NNCATGCATC C                        41

(2) INFORMATION FOR SEQ ID NO:9:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

CTACGTACNN NNNNNNNNNN NNNNNNNNNN NNGTACGTAG G                        41

(2) INFORMATION FOR SEQ ID NO:10:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:10:

CATGNNNNNN NNNNNNNNNN NNNNNNNNCA TGNNNNNNNN NNNNNNNNNN NNNNNNCATG    60

(2) INFORMATION FOR SEQ ID NO:11:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid
```

-continued (xi) SEQUENCE DESCRIPTION: SEQ ID NO:11:

GTACNNNNNN NNNNNNNNNN NNNNNNNNGT ACNNNNNNNN NNNNNNNNNN NNNNNNGTCC        60

(2) INFORMATION FOR SEQ ID NO:12:

(i) SEQUENCE CHARACTERISTICS:
        (A) LENGTH: 14 base pairs
        (B) TYPE: nucleic acid
        (C) STRANDEDNESS: single
        (D) TOPOLOGY: linear     (ii) MOLECULE TYPE: other nucleic acid     (xi) SEQUENCE DESCRIPTION: SEQ ID NO:12:

CTAGNNNNNN NNNN        14

(2) INFORMATION FOR SEQ ID NO:13:

(i) SEQUENCE CHARACTERISTICS:
        (A) LENGTH: 14 base pairs
        (B) TYPE: nucleic acid
        (C) STRANDEDNESS: single
        (D) TOPOLOGY: linear     (ii) MOLECULE TYPE: other nucleic acid     (xi) SEQUENCE DESCRIPTION: SEQ ID NO:13:

GATCNNNNNN NNNN        14